United States Patent [19]
Klein

[11] Patent Number: 5,482,030
[45] Date of Patent: Jan. 9, 1996

[54] AEROSOL AND NON-AEROSOL SPRAY COUNTER

[76] Inventor: David Klein, 190 Ross St., Apt. 1A, Brooklyn, N.Y. 11211

[21] Appl. No.: 259,195
[22] Filed: Jun. 13, 1994
[51] Int. Cl.⁶ .................................................. A61M 11/02
[52] U.S. Cl. .................. 128/200.23; 128/200.14; 128/200.18; 128/200.24; 128/205.23; 116/308
[58] Field of Search .................... 128/200.14, 200.18, 128/200.23, 200.24, 200.22, 205.23, 203.15; 116/308, DIG. 17

[56] References Cited

U.S. PATENT DOCUMENTS 4,668,218  5/1987  Virtanen .......................... 128/203.15
4,817,822  4/1989  Rand et al. ....................... 128/200.14
5,020,527  6/1991  Dessertine ........................ 128/205.23
5,284,133  2/1994  Burns et al. ...................... 128/200.14
5,363,842  11/1994 Mishelevich et al. ............ 128/205.23

*Primary Examiner*—Edgar S. Burr
*Assistant Examiner*—William J. Deane, Jr.
*Attorney, Agent, or Firm*—Michael I. Kroll

[57]  ABSTRACT

The present invention relates to an aerosol and non-aerosol spray counter whereby when a spray container is depressed, an automatic counting mechanism is activated.

1 Claim, 3 Drawing Sheets

AEROSOL AND NON-AEROSOL SPRAY COUNTER

BACKGROUND OF THE INVENTION

1. Field of the Invention

The present invention is directed to inhalers for the controlled inhalation of medication by a patient by self-activation. More particularly, it is directed to an inhaler which receives inhalation canisters for manual release of pressurized medication in spray form into the mouth and the inhaler is adapted to include a counting means to enhance proper self-administration of doses by patient.

The present invention generally relates to inhalation devices such as metered dose inhalers (MDIs), nebulizers, and dry powder inhalers. More particularly, the invention is directed to a dose controlled counting actuator that operates in conjunction with an inhalation device to prevent both patient under-compliance with prescribed medication dosing and patient abuse of or dependence on prescribed medication. Specifically, the invention contemplates the use of an actuator to prevent patient actuation of the inhalation device at non-prescribed intervals or at higher than prescribed doses.

2. Description of the Prior Art

Patient compliance with a doctor's instructions on prescribed medication is extremely important in the treatment of medical disorders. Although the rate of patient compliance is higher when he or she must return to the hospital or physician's office to receive the medication, most drug treatment regimens require the patient to administer the drugs at regular intervals without supervision by hospital personnel or the patient's physician or other qualified medical personnel. Obviously, the treatment of a medical disorder will be frustrated if the patient does not administer the drugs as prescribed. In the past, physicians have had to rely on the patient's self-interest in his or her own well being to assure that drugs are properly administered as scheduled.

With anti-anxiety or sedative/hypnotics, such as valium and barbiturates, it is widely recognized that there is a real possibility that the patient will abuse or become dependent on the drug. In Clinical Toxicology 8(5):495–513 (1975), it was argued that physicians should avoid the prescription of barbiturates because of the risk of dependence and the high toxicity of the drugs. Miller et al., American Family Physician v40, n4, p175(9) (October 1989), reported on the use of benzodiazepine drugs in the treatment of anxiety and particularly discussed the identification of dependence and addiction to these drugs. Bird, Northwest Medicine 69(8)533 (1970), reported on the problem of sedative overdose and suggested that sedatives should only be dispensed in small quantities and only on a restricted basis. Magnes, Applied Therapeutics (Toronto) 7:649 (1965) discussed the problems in the use of tranquilizing drugs in treating patients with psychoneuroses and demonstrated that in many patients treated with ethclorvynol an addiction develops.

Many drugs have a narrow therapeutic range and can have severe side effects. It is well recognized that controlling the dosing of these types of drugs is important in mitigating problems with side effects. Salzman, Hospital and Community Psychiatry (Washington) 33:2, 133–136 February 1982, reported that elderly patients are more susceptible to psychotropic drug toxicity, severe extrapyramidal side-effects from neuroleptics, and anticholinergic side-effects from tricyclic antidepressants. Milner, Medical Journal of Australia (Sydney) 2(3):153–155 (1969), reported that psychotropic drugs can have gastrointestinal side effects. Miller et al., American Family Physician v40, n4, p175(9) (October 1989), reported that benzodiazapine drugs pose adverse side effects to patients.

Many drugs can be extremely expensive (e.g., certain purified peptides and proteins). Controlling patient dosing of these drugs can have economic benefits.

An MDI typically comprises a canister under pressure fitted with a metering valve where the canister is filled with an aerosol formulation that includes a drug dissolved or dispersed in a propellant together with a surfactant. Nebulizers are devices which include mechanical or electronic devices (e.g., piezoelectric element) to atomize a drug suspension positioned in a containment cup. Nebulizers include an air or other gas source to deliver the atomized drug to the patient as a fine mist. Dry powder inhalers include mechanical or electronic devices to produce a fine mist from a powdered drug composition. MDIs, nebulizers, and dry powder inhalers have been used for many years to treat pulmonary disorders such as asthma. Examples of the types of drugs which have been routinely provided by these aerosolizing devices include: .beta.-agonists such as albuterol (salbutamol), isoproterenol, ephedrine, epinephrine, salmeterol, terbutaline; corticosteroids such as triamcinolone acetonide, beclomethasone diproprionate, dexamethasone, and aldosterone; allergic mediators such as cromclyn sodium; antibiotics; and anticholinergics.

Patient non-compliance with inhalation devices has been recognized as a major medical problem. In 1985, Dr. Spector reported in Spector, "Is your Asthmatic Patient Really Complying?", Annals of Allergy, 55:552–556 (1985), that patient compliance using a nebulizer to deliver lodoxamide, a cromolyn-like aerosol having a prophylactic (as opposed to immediate) bronchodilator effect, was extremely poor. In the investigation, patients were provided with a device called a Nebulizer Chronolog which contained a microswitch and timer that recorded the time of each use of the nebulizer. In addition, the patients were asked to record their use of the nebulizer in a diary. The patients were not told that the time of actuation of the nebulizer was also being automatically recorded. Over a several week study where lodoxamide was to be delivered at prescribed hourly intervals, it was determined from the automatically recorded usage data that all patients underdosed themselves. The mean rate of underusage was 48% for the study and the highest rate of underusage was 95.6%. Nevertheless, many patients did not tell the truth about their underusage in their diaries.

In a later study, Mawhinney et al., "Compliance in clinical trials of two nonbronchodilator, antiasthma medications", Annals of Allergy, 66:294–299 (1991), two groups of patients were provided with MDIs that were insertable into Nebulizer Chronolog devices (reported to be available from the ATA Corporation of Denver, Colo.). One group received either lodoxamide or placebo, while the other group received tixocortol pivalate or placebo. Even though patients were told they were being monitored, compliance was very low. Underusage was observed in a number of patients. In addition, overusage was observed in a number of patients, especially on days preceding follow up visits to the physicians office. In fact, only one patient in thirty four was found to be truly compliant.

There is a need to improve patient compliance with prescribed dosing schedules. As was reported in Nedelmann, Nervenarzt 53(1):33–38 (1982), it was reported that patient compliance with a doctor's drug prescription for psychotherapeutic drugs is only around 50%. Furthermore, Kahl et al., Public Health Reports Vol. v107, issue n1, page p37

(110) (January–February 1992) reported that overuse, underuse and inappropriate use of drugs by elderly patients are common problems. Several different solutions have been proposed for helping improve patient compliance. For example, Morris et al., Comprehensive Psychiatry 15(6):537–547 (1974), suggested that overdoses with the widely prescribed psychotherapeutic drugs may be avoided if there was a requirement of including an emetic or some other agent as a deterrent in the drugs, Witt, Dissertation Abstracts International 39(11):5321-B (1979) discusses the use of post-discharge pill count measurements, Beardsley, (Ph.D Dissertation University of Minn. 1977) reports a study that demonstrated increased compliance with a patient's increased knowledge about drugs gained by close interaction with pharmacists, and Venulet, Journal of Clinical Pharmacology and Biopharmacy (Munchen) 15(4):151–154 (1977), notes that having doctors understand the personality and sociocultural background of patients will aid in compliance. This invention is particularly directed to an improved inhalation device which aids in assuring patient compliance.

There is also a need for an inhalation device which can provide some assurance that a patient is not circumventing a dosing schedule by not inhaling medication. Mawhinney et al., Annals of Allergy, 66:294–299 (1991), points out that the Nebulizer Chronolog has no mechanism to determine whether a patient has activated the MDI without inhaling medication or how often they might have done so. Mawhinney et al. particularly note that Fox, Bull Int. Union Against Tuberculosis 32:307–331 (1961), reports that the self-administration of medicaments was studied in depth and it was particularly noted that home health visitors frequently found supplies of unused medications in a patient's home, despite finding a correct number of pills in the containers presented to the health investigators. Hence, there is a tendency of some patient's to "cheat" on dosing schedules. Preventing a patient's ability to "cheat" would help ensure compliance with prescribed dosing schedules.

As a result of suggestions made by one of the inventors, in consultations at Ft. Detrick, Md., scientists at the U.S. Army Medical Research Institute of Infectious Diseases in 1975 adapted a Collison nebulizer to deliver a continuous flow of small particle aerosols to mice infected with influenza virus. This system was described by Young and his associates in 1977 (Young, H. W., Dominik, J. W., Walker, J. S., Larson, E. W. Continuous aerosol therapy system using a modified Collison nebulizer. J Clin Microb 1977; 5(2):131–136). Several papers were published subsequently dealing with the use of this technology to treat influenza infections in mice with rimantadine (Stephen, E. L., Dominik, J. W., Moe, J. B., Spertzel, R. O., Walker, J. S. Treatment of influenza infection of mice by using rimantadine hydrochloride by the aerosol and intraperitoneal routes. Antimicrob Ag Chemother 1975; 8(2):154–158, amantadine and ribavirin Walker, J. S., Stephen, E. L., Spertzel, R. O. Small particle aerosols of antiviral compounds in treatment of type A influenza pneumonia in mice. J Infect Dis 1976; 133:A140–A144). Another study compared the effect of ribavirin given by the intraperitoneal and aerosol routes in influenza infections in mice (Stephen, E. L., Dominik, J. W., Moe, J. B., Walker, J. S. Therapeutic effects of ribavirin given by the intraperitoneal or aerosol route against influenza virus infections in mice. Antimicrob Ag Chemother 1976; 10(3):549–554) and on the physiological alterations in mice with influenza, untreated and treated with ribavirin aerosol (Arensman, J. B., Dominik, J. W., Hilmas, D. E. Effects of small particle aerosols of rimantadine and ribavirin on arterial blood pH and gas tensions and lung water content of A2 influenza-infected mice. Antimicrob Ag Chemother 1977; 12(1):40–46). Berendt and associates made further studies of treatment of influenza in mice with ribavirin aerosol (Berendt, R. F., Walker, J. S., Dominik, J. W., Stephen, E. L. Response of influenza virus-infected mice to selected doses of ribavirin administered intraperitoneally or by aerosol. Antimicrob Ag Chemother 1977; 11(6):1069–1070).

Based on the foregoing work, technology was adapted for human use by the inventor in his laboratory (Wilson, S. Z., Knight, V., Moore, R., and Larson, E. W. Amantadine small particle aerosol: generation and delivery to man. Proc Sol Exper Biol Med 1979; 161:350–354). Studies in mice in the inventor's laboratory confirmed the earlier results and, in addition, showed that a substantial therapeutic effect was demonstrable when treatment was delayed for as long as five days after inoculation (Knight, V., Wilson, S. Z., Wyde, P. R., Drake, S., Couch, R. B., Galegov, G. A., Novokhatsky, A. S. Small particle aerosols of amantadine and ribavirin in the treatment of influenza. In Ribavirin: A Broad Spectrum Antiviral Agent. Smith, R. A. and Kirkpatrick, W. (ed), Academic Press, Inc., New York 1980; pp. 129–145; Wilson, S. Z., Knight, V., Wyde, P. R., Drake, S., Couch, R. B. Amantadine and ribavirin aerosol treatment of influenza A and B infection in mice. Antimicrob Ag Chemother 1980; 17(4):642–648; Knight, V., Bloom, K., Wilson, S. Z., Wilson, R. K. Amantadine aerosol in humans. Antimicrob Ag Chemother 1979; 16(4):572–578). These studies additionally show that a combination of ribavirin and amantadine increase the effectiveness of therapy.

While the animal studies, in this case mice, demonstrated the efficacy of aerosol treatment, and encouraged human trial, the human trials were done with the realization that therapeutic effect, tolerance and toxicity may be quite different in man and animals. For example, in Wilson, et al, 1979, Amantadine Small Particle Aerosol: Generation and Delivery to Man, supra, in using the arbitrary criteria for retention of aerosol in mice and man, the estimated dosages in mice were approximate four-fold those in man when similar exposure periods were employed. Up until the present development, there was no determination made of the aerosol concentration of the drug which provided an effective, tolerant and nontoxic concentration for man. In addition, most available nebulizers provide coarse particles, that is particles having a mean diameter of 10 microns and over which are too coarse to penetrate effectively into the lungs.

While the small particle or nebulizer apparatus described and used in Wilson, et al, 1979, generated small particles and produced the results there set forth, it had the following disadvantages, (1) the valve from the bag to the mask would clog with precipitated drugs from the aerosol and the mere insertion of mechanical valves, however efficient, inevitably creates some obstruction that in some degree obstructs the flow of aerosol to the patient; (2) the air exhaled by the patient is forced into the aerosol stream flowing to the patient and the patient then inhales his own exhaled air from which the drug had been removed; and (3) the efficiency of the apparatus needed to be improved to provide a higher concentration of drug per liter of aerosol.

U.S. Pat. No. 4,211,711 is directed to ribavirin, and the small particle aerosol or nebulizer apparatus of this invention is particularly well suited to deliver small particle ribavirin for treatment of the respiratory tract including the lungs.

The most pertinent prior art relating to the present invention known to the applicant is the prior art set forth above in this section of the Background of the Invention.

In recent years, changes in living style have encouraged increasing numbers of homes to adopt the practice of spreading carpets directly on concrete or wooden floors, or first placing mats or highly hygroscopic tatamis (straw matting used as a floor covering) directly on such floors and then placing carpets on top of the mats or the tatamis. These floor coverings have fostered the growth of various species of acaroid mites, house dust mites, and cheyletidaes, which not only displease the inhabitants of the house, but also expose them to such diseases as allergic asthma and tetter. Wool carpets and mouton coverings become infested with case-bearing clothes moths and carpet beetles which live on animal hair. The larvae of these harmful insects hide deep in the roots of the carpet yarns, eat into such roots at random, and spoil the carpet's value.

The gradual elevation of living standards has given rise to frequent use of numerous types of agents for external application such as, for example, furniture cleaners, antistatic agents for clothes, phonographic records, and plastic articles, waterproofing agents and stain removers for clothes, softening agents and polishing agents for leather articles, fungistatic agents and deodorants for clothes and leather articles, flameretardants for curtains and wall papers, cleaners and defrosters for glass articles, rust-proofing lubricants for sliding doors, lubricants for various sliding surfaces, bactericidal deodorants for sick rooms and sick beds, repellents and insecticides for toy animals, agents for hair care, repellents and insecticides for stuffed animals, and detergents for carpets.

Heretofore, hand pumps and aerosol sprays have prevailed as the means for the application of such agents to carpets and other floor coverings. They, however, entail the following problems:

(1) These devices do not enable their contents, such as insecticides, to reach the roots of the carpet yarns. The contents thus applied, though effective from the preventive point of view, fail to produce the anticipated effects upon mites and harmful insects already inhabiting the carpet.

(2) Since the devices disperse their contents in the surrounding spaces, they may expose their users to the danger of inhaling noxious substances drifting in the air and suffering from loss of health.

(3) Since the devices inevitably permit dispersion of their contents during the course of application, part of the released agents which fail to land on the surfaces under treatment adhere to nearby furniture and fittings to stain their surfaces and smear their surroundings.

(4) When objects under treatment are not smooth flat surfaces, as in articles of felt, for example, the devices are incapable of enabling their contents to reach the roots of raised strings.

As one approach to the solution of these problems, furniture cleaners have been devised which have doughnut-shaped brush caps and sponge adapters fitted around injection spray nozzles. With these devices, users are allowed barely to spray their contents on the surfaces of given objects and then spread the contents deposited on the surfaces with the aid of brushes or sponges separately provided near the spray nozzles of the containers. Thus, these devices are still incapable of overcoming the problems (1)–(4) enumerated above. The surfaces effectively treated by these devices are limited in area and the released agents cannot be spread uniformly.

The use of inhalers is well known and the art has developed over the past twenty years to cover many versions of the basic concept of a "pumping" type medication applicator. The device is not truly pumped although a pumping like cycle is utilized. The medication is repeatedly released from a disposable canister, e.g. by depressions by the patient to create repeated sprays or inhalations as needed.

U.S. Pat. No. 3,361,306 to W. M. Grim illustrates a typical inhaler where a canister of medication is inserted into the back end of a device and the spray nozzle of the canister sits in a spray-directing member to shoot spray out of the front (mouth) end of the device when the canister is pressed down by a user.

U.S. Pat. No. 3,183,907 describes an inhaler in which a button on its underside is pushed by the user to release a controlled or metered amount of spray from a medication canister held in the top or back end of the inhaler.

U.S. Pat. No. 4,817,822 to Paul Rand et al describes an inhaler device which includes counting means for indicating the relative emptiness of a container or the number of doses dispensed. However, this inhaler counting mechanism is attached to the medicine container as well as the inhaler, such as by a retaining ring or retaining cap and is preferably not removed from the container.

Notwithstanding the prior art, the use of counters for an exact count of sprays per application, e.g. five sprays or six sprays each time the device is used, is not taught nor rendered obvious by the prior art, nor is the use of a timer to enable the user to control the elapsed time, e.g. 60 seconds, between each spray of a multispray application, as in the present invention.

Numerous innovations for an aerosol and non-aerosol spray counter have been provided in the prior art that are described as follows. Even though these innovations may be suitable for the specific individual purposes to which they address, they differ from the present invention as hereinafter contrasted.

U.S. Pat. No. 5,020,527

Inhaler Device with Counter/Timer Means

Pauline L. Dessertine

The present invention is directed to a device for inhaling medicine from an inhalation canister with a spray stem. It includes a hollow-bodied tubular main body having a back end adapted to receive an inhalation canister and a front end adapted for placement to or in a mouth, as well as a spray-directing element fixedly located within the main body, a counter and a timer. The spray-directing element has a continuous opening with an insert end for receiving a spray stem of an inhalation canister and a spray end for directing sprays of medicine through and out of the front end of the main body when an inhalation canister is activated by a user. The counter is connected to the main body for displaying a count of total activations of an inhalation canister and is advanced by each activation of an inhalation canister. The timer keeps track of time between inhalations for the user. Both the counter and the timer are resettable and are preferably electronic and may be contained in a single unit.

U.S. Pat. No. 4,969,854

Aerosol Applicator and Method

Yoshio Katsuda, Masuo Matsumoto,

Yoshihiro Minamite, Kazunori Hoshino,

Yukio Hachinohe, and Iwao Yazawa

Effective application of enough of the contents of an aerosol container to carpets and floor coverings to give thorough extermination of insects and mites infesting such floor coverings is accomplished by the method of this invention, comprising the steps of leading the contents from a stem to an applicator part formed on a lateral side of the aerosol container and allowing the contents to exude from an application face of the applicator part. This method is worked advantageously by an application type aerosol apparatus which comprises an applicator prop disposed in the vertical direction on the outside of the aerosol container, having the applicator part fixed in the longitudinal direction on the outer surface thereof, having a guide chamber for the contents of the aerosol solution formed on the inner surface of the applicator part and a guide inlet communicating with the stem of the aerosol container connected to the applicator prop and adapted to enable the incoming contents to exude from the outer surface of the applicator prop.

U.S. Pat. No. 4,733,984

Aerosol Applicator and Method

Yoshio Katsuda, Masuo Matsumoto, Yoshihiro Minamite,

Kazunori Hoshino, Yukio Hachinohe, and Iwao Yazawa

Effective application of enough of the contents of an aerosol container to carpets and floor coverings to give thorough extermination of insects and mites infesting such floor coverings is accomplished by the method of this invention, comprising the steps of leading the contents from a stem to an applicator part formed on a lateral side of the aerosol container and allowing the contents to exude from an application face of the applicator part. This method is worked advantageously by an application type aerosol apparatus which comprises an applicator prop disposed in the vertical direction on the outside of the aerosol container, having the applicator part fixed in the longitudinal direction on the outer surface thereof, having a guide chamber for the contents of the aerosol solution formed on the inner surface of the applicator part and a guide inlet communicating with the stem of the aerosol container connected to the applicator prop and adapted to enable the incoming contents to exude from the outer surface of the applicator prop.

U.S. Pat. No. 4,649,911

Small Particle Aerosol Generator for Treatment of Respiratory Disease Including the Lungs Jack V. Knight, and Samuel Z. Wilson Disclosed is a small particle aerosol or nebulizer apparatus effective for providing small particles of aerosol containing drug; that is, particles having a maximum diameter of 10 microns but predominantly 1–2 microns, effective for treating the respiratory tract and lungs and providing respiratory retention of most drugs of at least 50 milligrams up to about 100 milligrams per hour. It has features which result in more efficient output of aerosol containing drugs, provides very small aerosol particles which are readily deposited in the lower respiratory tract and lungs, and provides even flow of drug containing aerosol to a patient when exhaling and inhaling.

U.S. Pat. No. 5,284,133

Inhalation Device with a Dose-Timer, an Actuator Mechanism, and Patient Compliance Monitoring Means James S. Burns, and Daniel R. Marshak An inhalation device is provided with a mechanism to assure patient compliance with a drug dosage regimen. The control mechanism includes a controller (24), a timer (26), an actuator (28) and a signalling device (30). The controller (24) is programmed or preset with a time and dosage schedule for the drug to be delivered. For example, the controller (24) may be programmed to allow for two puffs from an MDI every eight hours. The actuator (28) operates in conjunction with the timer (26) and prevents the inhalation device from being actuated after the programmed dosage has been administered at the prescribed interval. The actuator (28) could be an electronically controlled valve (58) or pawl (66) arrangement or other suitable mechanism. The signaling device (30) provides an audible, visual or tactile sensation during the time period prescribed for administration of the drug so that the patient is reminded to inhale his or her medicine at the prescribed time intervals. The history of actuation, non-actuation, and improper attempts at actuation can all be recorded and analyzed off-site at a later by a physician, pharmacist, or other authorized health care professional.

Numerous innovations for an aerosol and non-aerosol spray counter have been provided in the prior art that are adapted to be used. Even though these innovations may be suitable for the specific individual purposes to which they address, they would not be suitable for the purposes of the present invention as heretofore described.

SUMMARY OF THE INVENTION

It is a main object of the present invention to automatically keep track of the quantity of uses to aid and insure the user that the user does not exceed the recommended quantity of the medicine.

It is a further main object of the present invention to automatically keep track of the number of uses to aid and insure that the user does not exceed the recommended number of uses of the medicine.

A still further object of the present invention is to automatically aid an permit the user to be aware of when to purchase additional quantities of medicine since the existing practice of simply shaking the container will not indicate to the user the remaining quantity of medicine left in the container.

The present invention is directed to a device for inhaling medicine from an inhalation canister with a spray stem. It includes a hollow-bodied tubular main body having a back end adapted to receive an inhalation canister and a front end adapted for placement to or in a mouth, as well as a spray-directing element fixedly located within the main body, a counter and a timer. The spray-directing element has a continuous opening with an insert end for receiving a spray stem of an inhalation canister and a spray end for directing sprays of medicine through and out of the front end of the main body when an inhalation canister is activated by a user. The counter is connected to the main body for displaying a count of total activations of an inhalation canister and is advanced by each activation of an inhalation canister. The counter is resettable and is preferably non-electronic and may be contained in a single unit being retrofittable to pre-existing inhalers.

In this embodiment of the invention, the application type aerosol apparatus specifically comprises a guide inlet connected to the stem of the aerosol container and opening into a trough-shaped receptacle frame closed at the opposite ends in the longitudinal direction thereof, and a flow space for the active agent interposed between the applicator part and the receptacle frame, so that the active agent brought in through the guide inlet will be allowed to exude from the outer face of the applicator prop.

All of the embodiments described above share the basic operating principle that the active agent held in the aerosol container is moved to an applicator part formed on the lateral side of the aerosol container and then is allowed to exude from the application face of the applicator part. The applicator part formed on the lateral side of the aerosol container and the guide means laid between the stem and the applicator part are not specifically limited in terms of shape.

The application apparatus of the present invention described above represents an entirely novel concept never anticipated by the conventional apparatus developed for the application of the contents of the aerosol container.

The other objects and characteristics of this invention will become apparent from the further disclosure of the invention to be made in the following detailed description of preferred embodiment, with reference to the accompanying drawings.

This invention further relates to an application type aerosol container which is used in effecting the aforementioned method for the application of the active agent, such as insecticide or miticide, held in the aerosol container.

In this embodiment of the invention, the application type aerosol apparatus specifically comprises a guide inlet connected to the stem of the aerosol container and opening into a trough-shaped receptacle frame closed at the opposite ends in the longitudinal direction thereof, an applicator part made of a non-absorbent material, having a smooth application face thereof protruding on one side and fitted fast in the receptacle frame, and a flow space for the active agent interposed between the applicator part and the receptacle frame, so that the active agent brought in through the guide inlet will be allowed to exude from the outer face of the applicator prop.

All of the embodiments described above share the basic operating principle that the active agent held in the aerosol container is moved to an applicator part formed on the lateral side of the aerosol container and then is allowed to exude from the application face of the applicator part. The applicator part formed on the lateral side of the aerosol container and the guide means laid between the stem and the applicator part are not specifically limited in terms of shape.

The application apparatus of the present invention described above represents an entirely novel concept never anticipated by the conventional apparatus developed for the application of the contents of the aerosol container.

The other objects and characteristics of this invention will become apparent from the further disclosure of the invention to be made in the following detailed description of preferred embodiment, with reference to the accompanying drawings.

The present invention is directed to improved apparatus which overcomes the above disadvantages and which provides continuous flow of small particle aerosol for treatment of diseases of the respiratory tract and the lung of man in which the drug is in concentrations which are effective and at the same time which man can tolerate, which are nontoxic for man and in which the drug is effectively deposited in the lungs. The aerosol or nebulizer apparatus of the present invention provides small particle aerosol to the patient. Advantageously, aerosol or nebulizer apparatus of the present invention has no valves or other obstructions to the free flow of aerosol to the patient which permits even flow of aerosol to the patient while inhaling and exhaling, thus, permitting the aerosol to readily penetrate into the lungs, the aerosol being hydrated by moisture in the respiratory tract and the lungs, and which provides substantially improved concentrations of drug per liter of aerosol.

The small particle aerosol or nebulizer apparatus is particularly effective in providing numbered doses of drug lower than usually required by oral or parenteral administration, thus reducing the risk of toxicity of larger doses but with the advantage of immediate deposition on the infected pulmonary surface.

Accordingly, it is an object of the present invention to provide an improved small particle aerosol generator or nebulizer effective for treatment of respiratory diseases with small particle aerosol concentrations of drugs which are therapeutically effective and safe in man.

It is a further object of the present invention to provide such an improved small particle aerosol generator or nebulizer by which diseases of the lung and respiratory tract in humans are treated by a continuous flows of small particle aerosol concentration of drugs sufficient for respiratory retention in man.

It is a further object of the present invention to provide an improved aerosol generator or nebulizer which produces a steady stream of small particles, that is, particles having a maximum diameter of 10 microns and predominately in the range of 1 to 2 microns by which drug aerosol concentrations for the treatment of diseases of the respiratory tract and lungs can be given safely and effectively.

A further object of the present invention is the provision of a small particle aerosol generator or nebulizer useful in the treatment of influenza virus infection in humans by inhalation of ribavirin, amantadine, or rimantadine, or mixtures thereof in small particle aerosol form in amounts or concentrations to be effective for treating influenza which the human can tolerate and which are safe to humans. By such improved small particle aerosol generator or nebulizer, ribavirin may also be provided to the patient in treatment of respiratory syncytial virus infections, parainfluenza virus infections, and other respiratory virus infections that are sensitive to the drug in vitro.

A further object of this invention is the provision of such a small particle aerosol generator or nebulizer which has no obstructions, such as valves, to a free flow of aerosol to the patient thereby avoiding clogging of the generator or nebulizer with precipitated aerosol.

A further object of the present invention is the provision of a small particle generator or nebulizer which provides an even flow of aerosol to the patient while the patient is inhaling and exhaling.

A further object of the present invention is the provision of a small particle generator or nebulizer in which the aerosol contains high concentrations of drugs.

Other and further objects, features and advantages appear throughout this specification and claims.

It is an object of this invention to provide a dose-timer and actuator mechanism for inhalation devices such as MDIs, nebulizers and dry powder inhalers, which promotes patient compliance.

It is another object of this invention to provide a dose counter and actuator mechanism that prevents abuse of addictive drugs by preventing too many actuations at a prescribed intervals and preventing additional actuations at non-prescribed intervals.

It is another object of this invention to provide a dose counter and actuator mechanism that helps promote the proper administration of drugs that are active within a narrow therapeutic range and helps control the dosing of expensive drugs.

It is another object of this invention to provide a dose counter and actuator mechanism that helps reduce under compliance to prescribed dosing schedules by signalling the patient during an interval when a dose is to be taken, if the patient has not inhaled his or her medication.

It is yet another object of this invention to provide a means for identifying when a patient is attempting to circumvent a dosing schedule for an inhalation device.

According to the invention, a control unit is either built-in or attached to an inhalation device. The control unit is either programmed or preset according to a prescribed dosing regimen for a particular drug to be administered. A counter is associated with the control unit and activates a counter display device if the patient does not actuate the inhalation device a programmed number of times within a preset time period at the prescribed dosing period. The counter may be set or programmed to be actuated, thereby allowing the patient to actuate the device in a timely manner without being subjected to overdosing.

A locking mechanism is preferably associated with the control unit and prevents the actuation of the inhalation device at non-prescribed intervals and prevents more than the prescribed number of doses to be administered at any particular dosing period. A recording device could be connected to the control unit so that the time and number of actuations of the inhalation could be recorded for later analysis. In addition, attempted actuations that were prevented by the locking mechanism could be recorded so that a patient's tendency towards dependency could be identified early in the treatment.

Accordingly, it is an object of the present invention to provide an aerosol and non-aerosol spray counter with a counter built in enabling the user to know his amount of dosing and approximately when to buy a new spray.

More particularly, it is an object of the present invention to provide an aerosol and non-aerosol spray counter with a counter built in which when the aerosol bottle is pushed in the counter automatically activates, thus, displaying the current number of doses.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawing.

DETAILED DESCRIPTION OF THE PREFERRED EMBODIMENT

Figure 1:
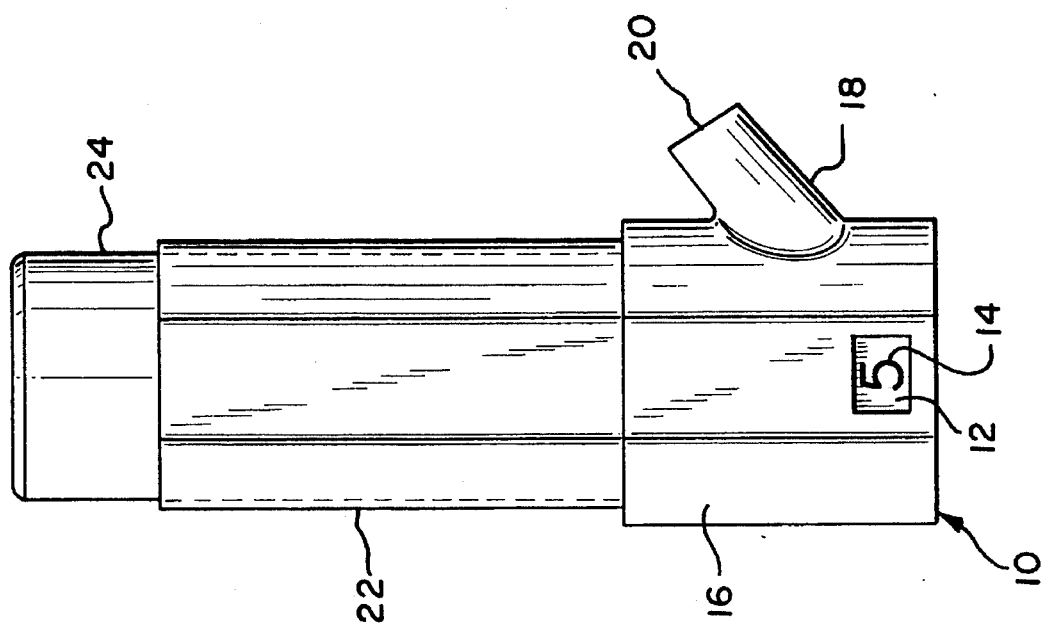
FIG. 1 is a side view of a spray counter exhibiting the following features; counter disk, counter number, counter housing, egress nozzle, nozzle opening, spray container housing, and spray container.

First, referring to FIG. 1 which is a side view of a spray counter 10 exhibiting the following features; counter disk 12, counter number 14, counter housing 16, egress nozzle 18, nozzle opening 20, spray container housing 22, and spray container 24.

Figure 2:
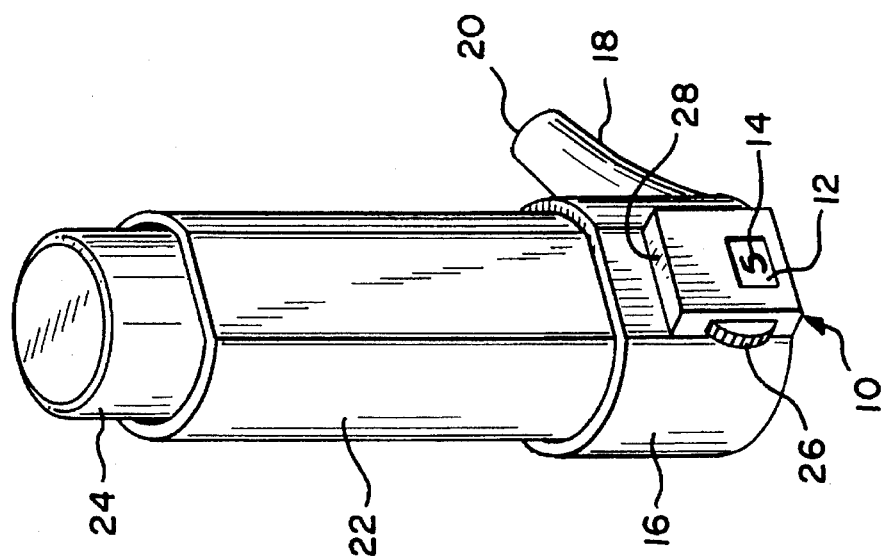
FIG. 2 is a perspective view of a spray counter exhibiting the following features; counter disk, counter number, counter housing, egress nozzle, nozzle opening, spray container housing, and spray container.

Now referring to FIG. 2 which is a perspective view of a spray counter 10 exhibiting the following features; counter disk 12, counter number 14, counter housing 16, egress nozzle 18, nozzle opening 20, spray container housing 22, and spray container 24. The counter disk 12 can be reset and "zeroed" by spinning said disk 12 utilizing the counter disk friction means 26.

Figure 3:
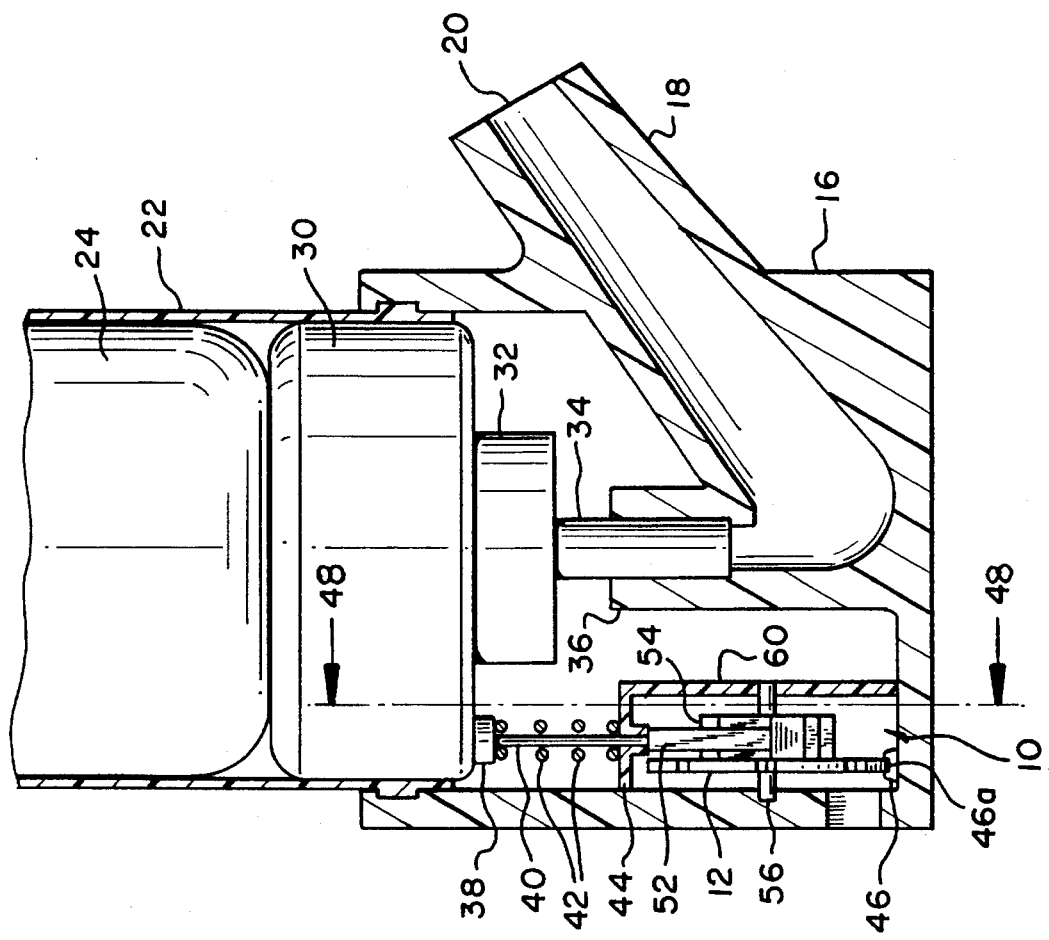
FIG. 3 is a cross sectional side view of a spray counter exhibiting the following features; counter disk, counter housing, egress nozzle, nozzle opening, spray container housing, spray container, spray container top, spray container spout top, spray container spout, counter housing spray container spout receptacle, counter plunger distal end, counter plunger, counter plunger rollers, counter disk housing top, counter disk rotation stopper, counter disk rotation stopper indents, cross section cut, counter plunger rotating shaft, counter disk rotating means, axle, and counter disk housing rear wall.

Now referring to FIG. 3 which is a cross sectional side view of a spray counter 10 exhibiting the following features; counter disk 12, counter housing 16, egress nozzle 18, nozzle opening 20, spray container housing 22, spray container 24, spray container top 30, spray container spout top 32, spray container spout 34, counter housing spray container spout receptacle 36, counter plunger distal end 38, counter plunger 40, counter plunger rollers 42, counter disk housing top 44, counter disk rotation stopper 46, counter disk rotation stopper indents 46A, cross section cut 48, counter plunger rotating shaft 52, counter disk rotating means 54, axle 56, and counter disk housing rear wall 60.

Figure 4:
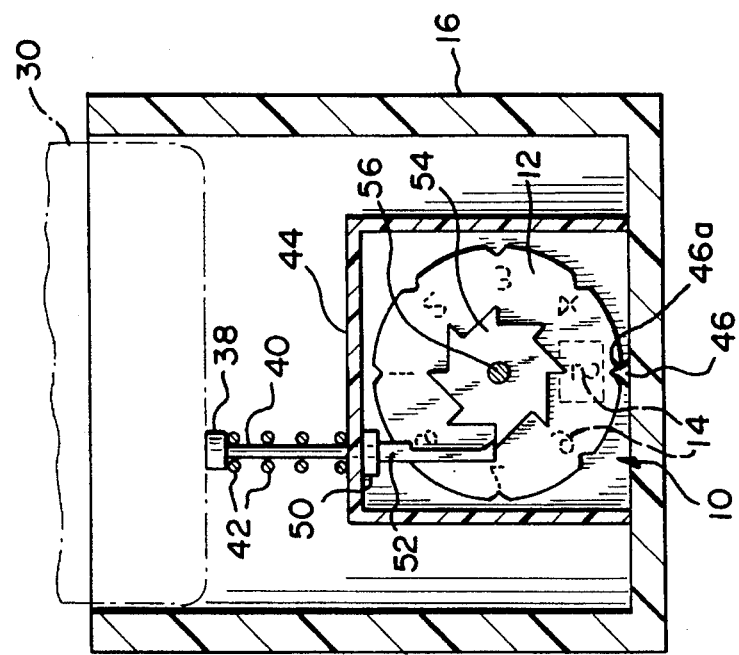
FIG. 4 is cross sectional rear view of a counter disk exhibiting the following features; counter number, counter housing, spray container top, counter plunger, counter plunger rollers, counter disk housing top, counter disk rotation stopper, counter disk rotation stopper indents, counter plunger washer, counter plunger rotating shaft, counter disk rotating means, and axle.

Now referring to FIG. 4 which is cross sectional rear view of a spray counter 10 exhibiting the following features; counter disk 12 exhibiting the following features; counter number 14, counter housing 16, spray container top 30, counter plunger 40, counter plunger rollers 42, counter disk housing top 44, counter disk rotation stopper 46, counter disk rotation stopper indents 46A, counter plunger washer 50, counter plunger rotating shaft 52, counter disk rotating means 54, and axle 56. When the spray container 24 is depressed, the counter plunger distal end 38 which protrudes through the counter disk housing top 44 which is concurrently depressed transmitting energy to the counter plunger 40 guided on the counter plunger rollers 42 having a counter plunger washer 50. The counter disk 14 rotates until counter disk rotation stopper 46 upon the counter plunger rotating shaft 52 depressing the counter disk rotating means 54 until said counter disk 12 stops at the counter disk rotation stopper indents 46A, thus, displaying a number 14 representing the number of sprays taken thereof. Said spray counter 10 automatically returns to a pre-counting position after depression pressure is released.

Figure 5:
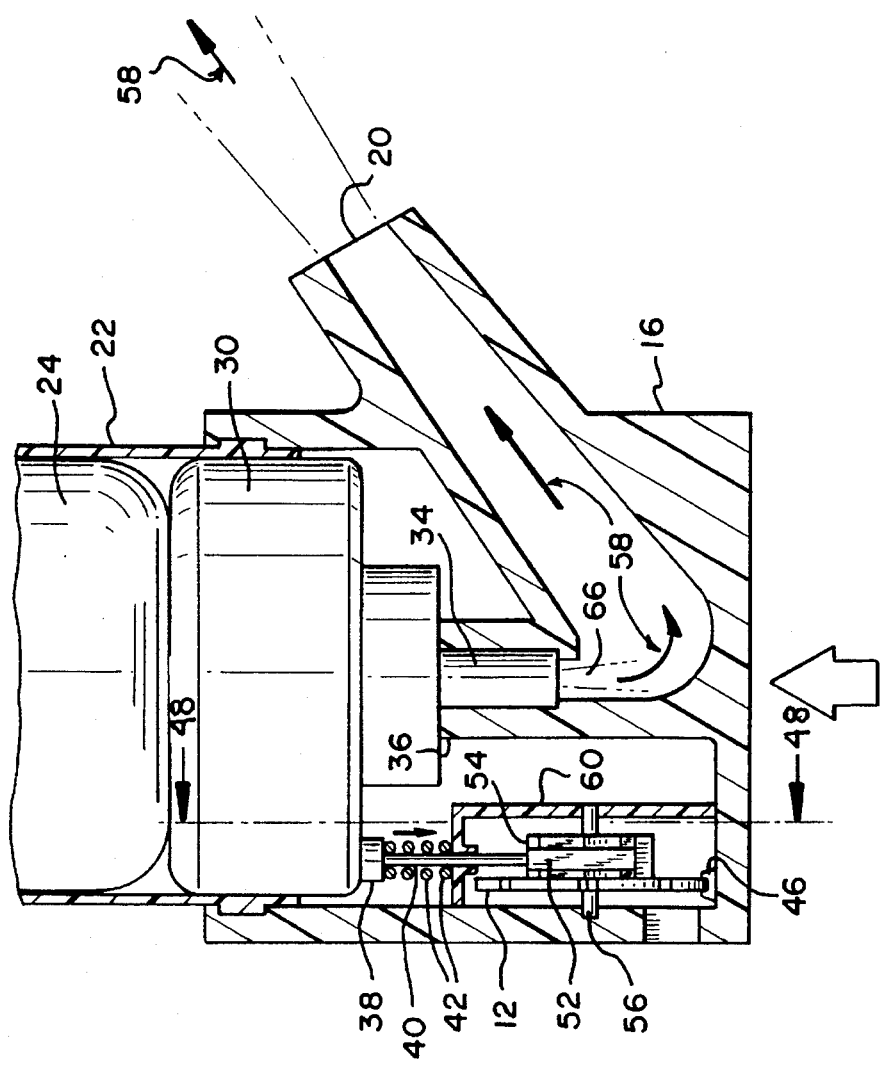
FIG. 5 is a cross sectional side view of a spray counter releasing spray exhibiting the following features; counter disk, counter housing, egress nozzle, nozzle opening, spray container housing, spray container, spray container top, spray container spout top, spray container spout, counter housing spray container spout receptacle, counter plunger distal end, counter plunger, counter plunger rollers, counter disk housing top, counter disk rotation stopper, counter disk rotation stopper indents, cross section cut, counter plunger rotating shaft, counter disk rotating means, axle, spray direction, counter disk housing rear wall, and counter plunger direction of movement.

Now referring to FIG. 5 which is a cross sectional side view of a spray counter 10 releasing spray exhibiting the following features; counter disk 12, counter housing 16, egress nozzle 18, nozzle opening 20, spray container housing 22, spray container 24, spray container top 30, spray container spout top 32, spray container spout 34, counter housing spray container spout receptacle 36, counter plunger distal end 38, counter plunger 40, counter plunger rollers 42, counter disk housing top 44, counter disk rotation stopper 46, counter disk rotation stopper indents 46A, cross section cut 48, counter plunger rotating shaft 52, counter disk rotating means 54, axle 56, spray direction 58, counter disk housing rear wall 60, and counter plunger direction of movement 62.

Figure 6:
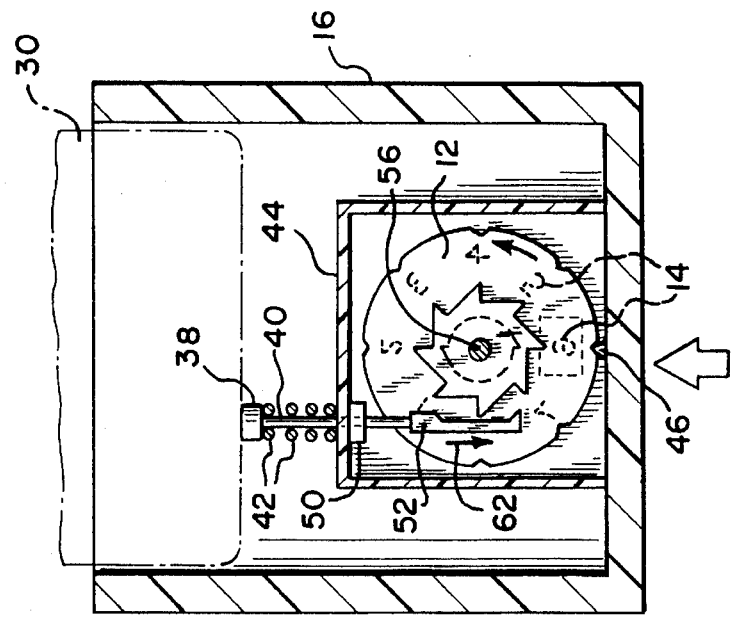
FIG. 6 is cross sectional rear view of a counter disk exhibiting the following features; counter number, counter housing, spray container top, counter plunger, counter plunger rollers, counter disk housing top, counter disk rotation stopper, counter disk rotation stopper indents, counter plunger washer, counter plunger rotating shaft, counter disk rotating means, axle, and counter plunger direction of movement.

Lastly, referring to FIG. 6 which is a cross sectional rear view of a spray counter 10 exhibiting the following features; counter disk 12, counter number 14, counter housing 16, spray container top 30, counter plunger 40, counter plunger rollers 42, counter disk housing top 44, counter disk rotation stopper 46, counter disk rotation stopper indents 46A, counter plunger washer 50, counter plunger rotating shaft 52, counter disk rotating means 54, axial 56, and counter plunger direction of movement 62.

It will be understood that each of the elements described above, or two or more together, may also find a useful application in other types of constructions differing from the type described above.

While the invention has been illustrated and described as embodied in a spray counter, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. An aerosol and non-aerosol spray counter comprising:

a) a counter housing, at least one spray container housing for receiving a standard size spray container therein, at least one counter disk housing further comprising a counter disk housing top and at least one counter disk housing rear wall, at least one counter housing spray container spout receptacle capable of receiving a spout of a standard size spray container, at least one egress nozzle through which spray can exit a nozzle opening at a distal end therein, and b) at least one manually operated counting means comprising a counter disk having a plurality of numbers thereon, means comprising a finger operated wheel enabling a user to reset set counting means, a counter plunger with a distal end, counter plunger rollers, a counter plunger washer, said counter plunger contacting a counter plunger shaft, a counter disk rotating means directly connected to said counter disk so that when said spray container is depressed, said counter plunger distal end upon being depressed transmitting energy to said counter plunger with said counter plunger washer thereon which is guided within said counter rollers further transmitting energy to said counter shaft which depresses said counter rotating means thereby rotating said counter disk exhibiting said sequential counter numbers correlating to a number of sprays, said counter disk having a plurality of counter disk rotation stopper indents corresponding to said counter numbers, and at least one counter disk rotation stopper attached to said disk housing, and cooperating with said indents whereby when a spray container is depressed, said counting means self activates, thus, counting the number of times said spray has been discharged therethrough.

* * * * *